US011103297B2

(12) United States Patent
Suzuki et al.

(10) Patent No.: US 11,103,297 B2
(45) Date of Patent: Aug. 31, 2021

(54) MEDICAL DEVICE AND MEDICAL SYSTEM

(71) Applicant: OLYMPUS CORPORATION, Hachioji (JP)

(72) Inventors: Tatsuya Suzuki, Hachioji (JP); Ko Kawashima, Musashino (JP); Yuichi Shintomi, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 848 days.

(21) Appl. No.: 15/912,288

(22) Filed: Mar. 5, 2018

(65) Prior Publication Data
US 2018/0193081 A1    Jul. 12, 2018

Related U.S. Application Data

(63) Continuation of application No. PCT/JP2016/074837, filed on Aug. 25, 2016.

(30) Foreign Application Priority Data

Sep. 3, 2015   (JP) .............................. JP2015-173751

(51) Int. Cl.
*A61B 18/14*   (2006.01)
*A61N 7/02*   (2006.01)
(Continued)

(52) U.S. Cl.
CPC .... *A61B 18/082* (2013.01); *A61B 17/320092* (2013.01); *A61B 18/14* (2013.01);
(Continued)

(58) Field of Classification Search
CPC ........... A61B 2018/00589; A61B 2018/00607; A61B 2018/0063; A61B 2018/0094;
(Continued)

(56) References Cited

U.S. PATENT DOCUMENTS

2012/0221004 A1* 8/2012 Kerr .................. A61B 18/1206
606/51

FOREIGN PATENT DOCUMENTS

JP     S63-230142 A    9/1988
JP     H03-49729 A    3/1991
(Continued)

OTHER PUBLICATIONS

Jul. 4, 2017 Japanese Office Action issued in Patent Application No. 2017-528606.
(Continued)

*Primary Examiner* — Michael F Peffley
*Assistant Examiner* — Samantha M Good
(74) *Attorney, Agent, or Firm* — Oliff PLC

(57) ABSTRACT

A medical device includes: a housing; a switch provided on the housing; and a converter provided in the housing. The switch is configured to allow switching between a plurality of states and is configured to output a first signal in response to one of the states to which the switching is performed. The converter is configured to convert the first signal into a second signal of a different system when the converter receives the output of the first signal, and is configured to output the second signal to an outside configured to detect the second signal.

12 Claims, 8 Drawing Sheets

(51) Int. Cl.
*A61B 18/08* (2006.01)
*A61B 17/32* (2006.01)
*A61N 7/00* (2006.01)
*A61B 17/00* (2006.01)
*A61B 18/00* (2006.01)
*A61B 18/12* (2006.01)
*A61B 17/068* (2006.01)

(52) U.S. Cl.
CPC ............ *A61B 18/1442* (2013.01); *A61N 7/00* (2013.01); *A61N 7/02* (2013.01); *A61B 17/068* (2013.01); *A61B 18/1206* (2013.01); *A61B 18/1477* (2013.01); *A61B 2017/00017* (2013.01); *A61B 2017/00367* (2013.01); *A61B 2018/0019* (2013.01); *A61B 2018/0063* (2013.01); *A61B 2018/0094* (2013.01); *A61B 2018/00404* (2013.01); *A61B 2018/00589* (2013.01); *A61B 2018/00607* (2013.01); *A61B 2018/00922* (2013.01); *A61B 2018/00928* (2013.01); *A61B 2018/00958* (2013.01)

(58) Field of Classification Search
CPC ........ A61B 2018/00958; A61B 18/082; A61B 18/14; A61B 18/1442; A61B 18/1206; A61B 18/1477; A61B 17/068; A61B 2018/00404; A61N 7/00; A61N 7/02; H01H 3/00
See application file for complete search history.

(56) References Cited

FOREIGN PATENT DOCUMENTS

| | | |
|---|---|---|
| JP | 3197268 B2 | 8/2001 |
| JP | 2005-230062 A | 9/2005 |
| JP | 2006-288431 A | 10/2006 |
| WO | 2015/122308 A1 | 8/2015 |

OTHER PUBLICATIONS

Dec. 6, 2016 International Search Report issued in International Patent Application No. PCT/JP2016/074837.

Mar. 6, 2018 International Preliminary Report on Patentability issued in International Application No. PCT/JP2016/074837.

\* cited by examiner

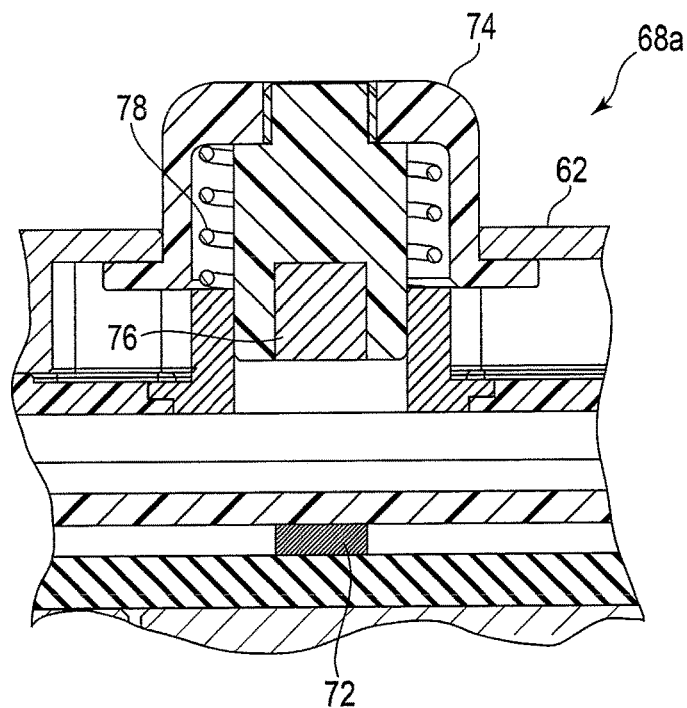
F I G. 3A
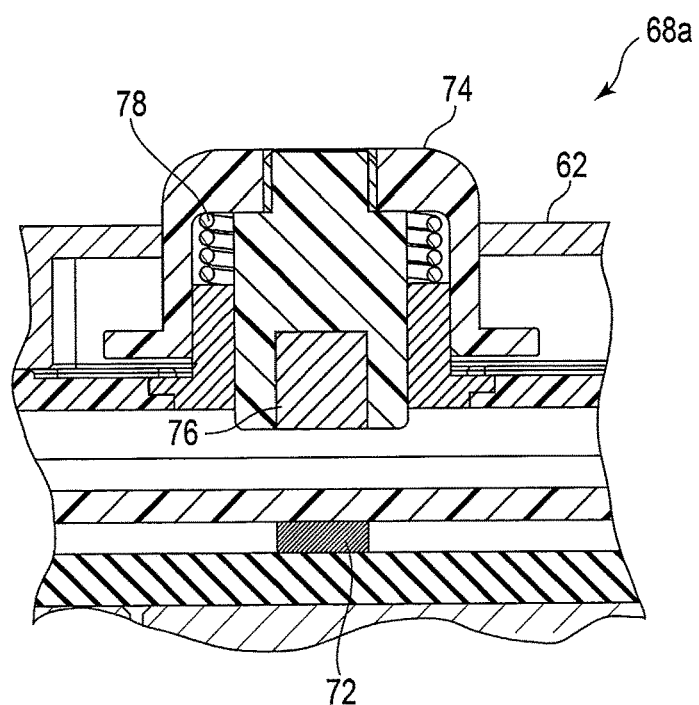
F I G. 3B

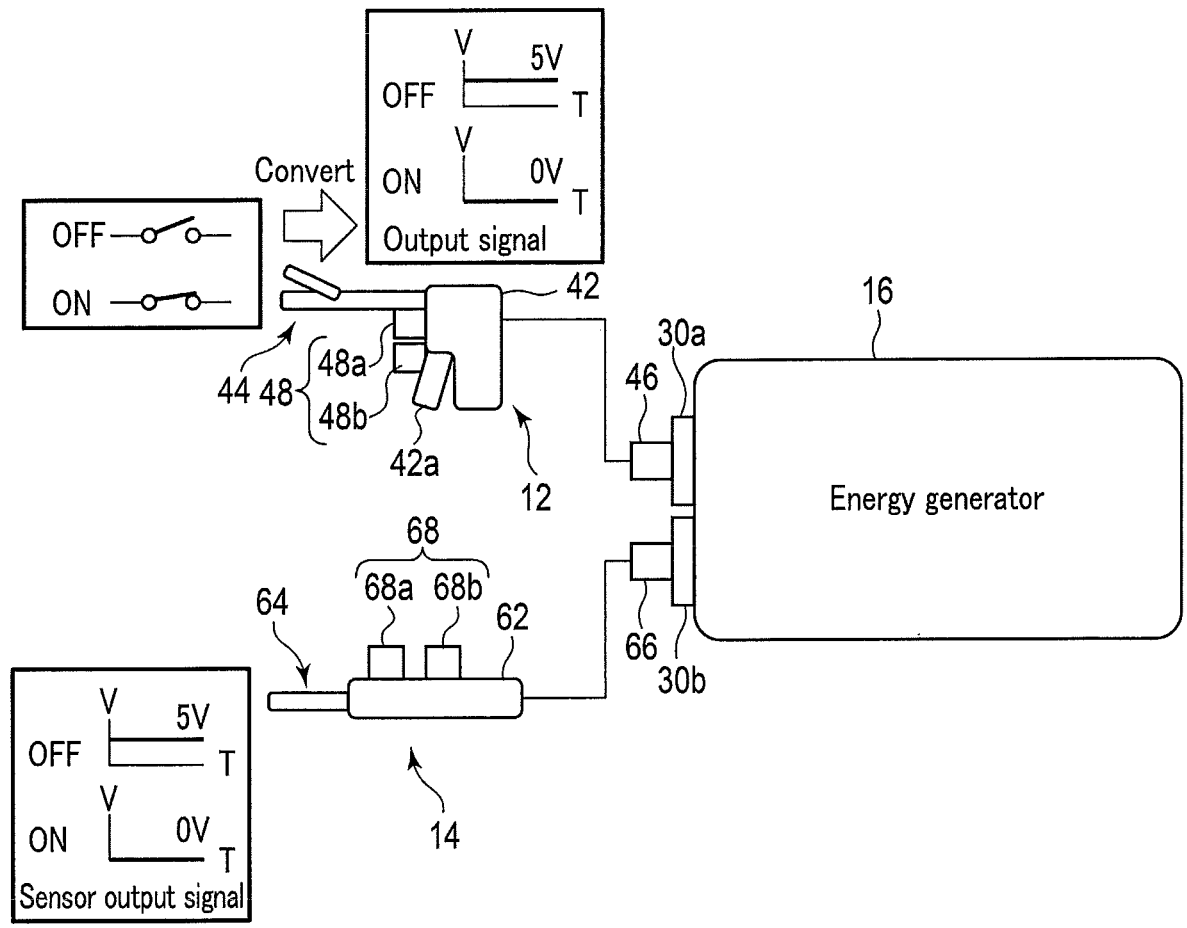
F I G. 9

MEDICAL DEVICE AND MEDICAL SYSTEM

CROSS-REFERENCE TO RELATED APPLICATIONS

This application is a Continuation Application of PCT Application No. PCT/JP2016/074837, filed Aug. 25, 2016 and based upon and claiming the benefit of priority from prior Japanese Patent Application No. 2015-173751, filed Sep. 3, 2015, the entire contents of all of which are incorporated herein by reference.

BACKGROUND OF THE INVENTION

1. Field of the Invention

The present invention relates to a medical device and a medical system.

2. Description of Related Art

A medical device that includes one or more switches is known, as disclosed in, for example, Jpn. Pat. Appln. KOKAI Publication No. 2006-288431. The medical device uses a switch detector provided in a generator that is provided separately from the medical device to detect switching between ON and OFF of a mechanical or sensor switch.

BRIEF SUMMARY OF THE INVENTION

According to one aspect of the present invention, a medical device includes: a housing; a switch provided on the housing, and the switch being configured to allow switching between a plurality of states and being configured to output a first signal in response to one of the states to which the switching is performed; and a converter provided in the housing, the converter being configured to convert the first signal into a second signal of a different system when the converter receives the output of the first signal, and being configured to output the second signal to an outside configured to detect the second signal.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 3A is a vertical cross-sectional view schematically showing an example of a sensor switch used in a treatment instrument of the medical system in an OFF state, in particular, according to the first embodiment and a second embodiment.

FIG. 3B is a vertical cross-sectional view schematically showing an example of the sensor switch used in the treatment instrument of the medical system in an ON state, in particular, according to the first and second embodiments.

FIG. 9 is a schematic diagram showing a medical system according to the second embodiment.

DETAILED DESCRIPTION OF THE INVENTION

Hereinafter, embodiments of the present invention will be described with reference to the accompanying drawings.

First Embodiment

A first embodiment will be explained with reference to FIGS. 1 to 5.

Figure 1:
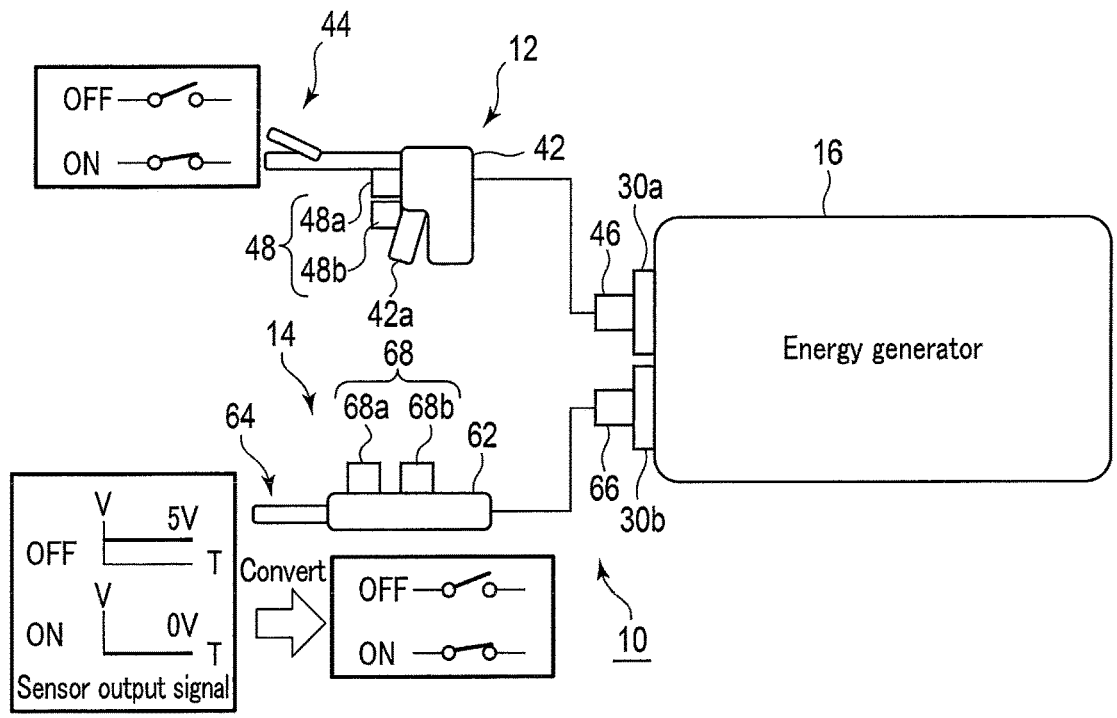
FIG. 1 is a schematic diagram showing a medical system according to a first embodiment.

As shown in FIG. 1, a medical system 10 according to the present embodiment includes a first treatment instrument (clamping device) 12 that serves as a medical device, a second treatment instrument (pencil-shaped device) 14 that serves as another medical device, and an energy generator (energy controller) 16. In the medical system 10 according to the present embodiment, the first treatment instrument 12 and the second treatment instrument 14, for example, can be simultaneously used. It is preferable that each of the first treatment instrument 12 and the second treatment instrument 14 can be gripped by a user's hand when operated. In the description that follows, let us assume that a clamping device that clamps a living tissue is used as an example of the first treatment instrument 12, and a pencil-shaped device that is gripped by a user like a pen to treat a living tissue is used as an example of the second treatment instrument 14. A description will be given about a treatment that uses the first treatment instrument 12 and the second treatment instrument 14, in particular, a treatment that uses ultrasonic vibration and/or a high-frequency current, which is performed in response to pushing of switches that will be described later. The first treatment instrument 12 and the second treatment instrument 14 may produce a heat-transfer effect on the living tissue using a heating element or eject a staple in response to pushing of switches that will be described later, and are configured to provide a suitable treatment in response to the pushing of the switches.

Figure 2:
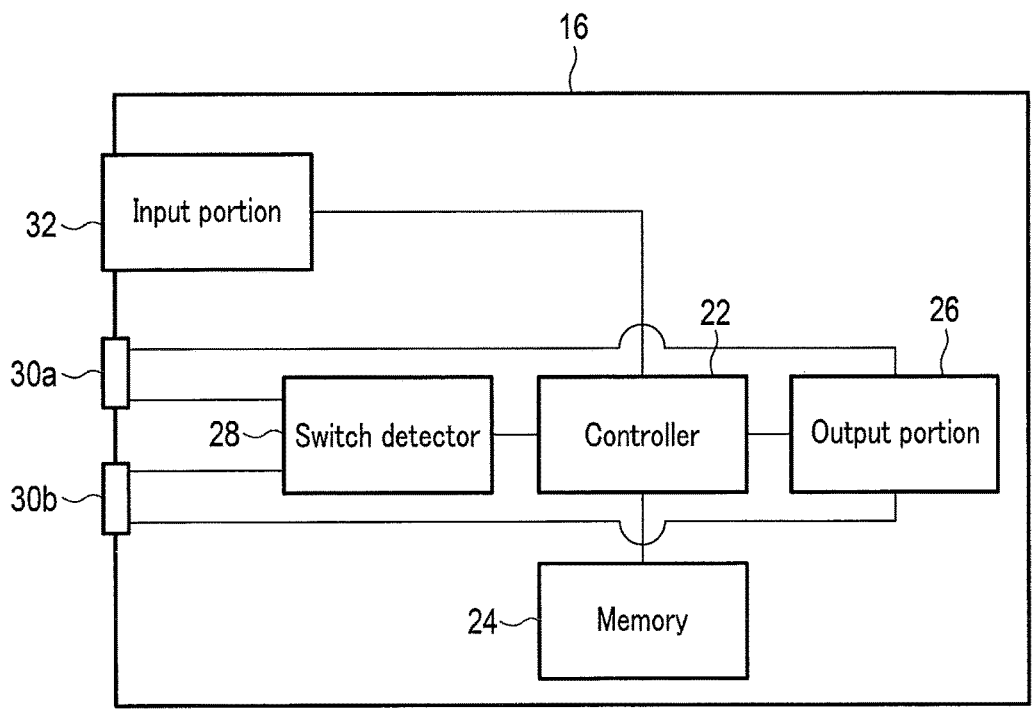
FIG. 2 is a schematic block diagram showing an energy generator of a medical system according to the first and second embodiments.

As shown in FIG. 2, the energy generator 16 includes a controller (control circuit) 22, a memory 24, an energy output portion (energy generating circuit) 26, a switch detector (switch detecting circuit) 28, a plurality of female connectors 30a and 30b, and an input portion 32. It is preferable that the plurality of female connectors 30a and 30b are under the same standard. The plurality of female connectors 30a and 30b are configured in such a manner that the treatment instruments 12 and 14 can be simultaneously connected to the energy generator 16. The female connectors 30a and 30b are connected to a switch detector 28. The switch detector 28 is connected to a controller (processor) 22. The input portion 32 is configured to make various settings, such as setting of an output level of an ultrasonic output, setting of an output intensity of a high-frequency current, setting of functions of switches 48a, 48b, 68a, and 68b, which will be described below, and the input content is stored in the memory 24. The controller 22 is connected to an energy output portion 26, and controls the output of energy from the energy output portion 26. The energy output portion 26 is connected to the female connectors 30a and 30b. The energy output portion 26 is capable of supplying a suitable amount of energy to the first treatment instrument 12 and the second treatment instrument 14, on the basis of the content set in the memory 24.

As shown in FIG. 1, the first treatment instrument 12 includes a housing 42 that includes a movable handle 42a, a treatment portion 44 that extends from the housing 42 and that is configured to clamp a living tissue depending on an operation of the movable handle 42a, and a connector 46 that extends on a side opposite to the treatment portion 44 from the housing 42.

The first treatment instrument 12 includes a switch unit (switch) 48 including a first switch 48a and a second switch 48b. In the description that follows, let us assume that mechanical switches are used as the first switch 48a and the second switch 48b. Mechanical switches such as the first mechanical switch 48a and the second mechanical switch 48b are configured in such a manner that a state can be selected from a plurality of states (switching can be performed between a plurality of states, which are two states in this case: ON and OFF). The connector 46 respectively inputs an operation signal of the first mechanical switch 48a and the second mechanical switch 48b to the energy generator 16 via the female connector 30a, and transmits an energy output from the output portion 26 of the energy generator 16 to the treatment portion 44. When the connector 46 is connected to the female connector 30a of the energy generator 16, the energy generator 16 recognizes that the first treatment instrument 12 is connected, and functions of the first mechanical switch 48a and the second mechanical switch 48b are stored in the memory 24 of the energy generator 16. The functions of the first mechanical switch 48a and the second mechanical switch 48b may be stored in the memory 24 on the basis of the input to the input portion 32 of the energy generator 16.

As an example, when the first mechanical switch 48a is pushed by the user, energy is supplied from the energy generator 16 to the treatment portion 44. The treatment portion 44 makes a bipolar high-frequency output to a clamped living tissue, and coagulates (seals) the living tissue in a seal mode. When the second mechanical switch 48b is pushed by the user, energy is supplied from the energy generator 16 to the treatment portion 44. The treatment portion 44 simultaneously performs an ultrasonic output and a bipolar high-frequency output to the clamped living tissue, and coagulates (seals) and dissects the living tissue in a seal-and-cut mode.

In the first treatment instrument 12, the direction of operation of the first mechanical switch 48a and the second mechanical switch 48b and the direction of extension of the treatment portion 44 relative to the housing 42 are substantially equal. In this case, when the operator operates the first mechanical switch 48a or the second mechanical switch 48b while gripping the movable handle 42a, the position of the treatment portion 44, namely, the position of the treatment portion 44 relative to the position of a living tissue or a blood vessel, is not easily shifted. It is thus preferable that mechanical switches such as the first mechanical switch 48a and the second mechanical switch 48b are used in a clamping device.

In the present embodiment, let us assume that the switch detector 28 shown in FIG. 2 is capable of directly detecting switching (a second signal) of mechanical switches 48a and 48b shown in FIG. 1. The switch detector 28 of the energy generator 16 according to the present embodiment may include, for example, a photocoupler (not shown). When the first mechanical switch 48a is pushed and switched to ON, for example, a closed circuit is formed, and a current flows from the first mechanical switch 48a to the photocoupler as a signal (second signal). Since such a technique is widely known in the art, a detailed explanation thereof will be omitted. Thus, a light-emitting diode of the photocoupler emits light, a photodiode of the photocoupler receives the light, and a signal output from the photodiode is determined by the controller 22. That is, when the first mechanical switch 48a is pushed and switched to ON, the switch detector 28 receives a signal (second signal) output from the first treatment instrument 12, and detects the received signal. The signal (ON information) is transmitted from the switch detector 28 to the controller 22. When the first mechanical switch 48a is switched to OFF, the switch detector 28 receives a signal (second signal) output from the first treatment instrument 12, and detects the received signal. The signal (OFF information) is then transmitted from the switch detector 28 to the controller 22.

In this manner, the switch detector 28 is capable of detecting a signal in response to an operation on the first mechanical switch 48a. Similarly, a signal can be detected in response to an operation on the second mechanical switch 48b; however, an explanation thereof will be omitted. Thus, the energy generator 16 is capable of outputting a suitable amount of energy in response to an operation on the first mechanical switch 48a and the second mechanical switch 48b of the first treatment instrument 12. Accordingly, when the first mechanical switch 48a of the first treatment instrument 12 is pushed, energy is transmitted to the treatment portion 44 in a seal mode, and when the second mechanical switch 48b is pushed, energy is transmitted to the treatment portion 44 in a seal-and-cut mode.

As shown in FIG. 1, the second treatment instrument 14 includes a cylindrical housing 62 that is gripped like a pen, a treatment portion 64 that extends from the housing 62, and a connector 66 that extends toward a side different from the treatment portion 64 from the housing 62.

The second treatment instrument 14 includes a switch unit (switch) 68 including a first switch 68a and a second switch 68b. In the description that follows, let us assume that a sensor switch is used as each of the first switch 68a and the second switch 68b. The connector 66 respectively converts an operation signal of the first sensor switch 68a and the second sensor switch 68b using a signal converter (signal conversion circuit) 82, inputs the converted operation signal to the energy generator 16 via the female connector 30b, and transmits an energy output from the output portion 26 to the treatment portion 64. When the connector 66 is connected to the female connector 30b of the energy generator 16, it is recognized that the second treatment instrument 14 is connected to the energy generator 16, and functions of the first sensor switch 68a and the second sensor switch 68b are stored in the memory 24 of the energy generator 16. The functions of the first sensor switch 68a and the second sensor switch 68b may be stored in the memory 24 on the basis of the input to the input portion 32 of the energy generator 16.

As an example, when the first sensor switch 68a is pushed by the user, a monopolar high-frequency output is made to the living tissue that has contacted the treatment portion 64 at a distal end of the treatment instrument 14, using the energy supplied from the energy generator 16, and the living tissue is dissected. When the second sensor switch 68b is pushed by the user, a high-frequency output and a monopolar high-frequency output are simultaneously made to the living tissue that has contacted the treatment portion 64 at a distal end of the treatment instrument 14, using the energy supplied from the energy generator 16, and the living tissue is dissected. The dissection performance differs between the case where the first sensor switch 68a is pushed and the second sensor switch 68b is pushed.

The sensor switches such as the first sensor switch 68a and the second sensor switch 68b are configured in such a manner that a state can be selected from a plurality of states (switching can be performed between a plurality of states, which are two states in this case: ON and OFF), using a small amount of power, compared to the mechanical switches 48a and 48b, by selection of a spring, for example. In the second treatment instrument 14, the direction of operation of the first and second sensor switches 68a and 68b and the direction of extension of the treatment portion 64 relative to the gripping position of the housing 62 are substantially orthogonal. Thus, when the first sensor switch 68a or the second sensor switch 68b is operated, the position of the treatment portion 64, namely, the position of the living tissue is not easily shifted, compared to when a mechanical switch is operated. Accordingly, it is preferable that the first sensor switch 68a and the second sensor switch 68b are used for a pencil-type device, which needs to suppress a positional shift of the treatment portion 64.

As shown in FIGS. 3A and 3B, the first sensor switch 68a includes a detector (sensor) 72 and a push button (input portion) 74. The detector 72 is provided in the housing 62 and the push button 74 is provided on the housing 62. Here, the detector 72 converts the amount of change in physical quantity detected by the detector 72 into an amount of voltage as an electric signal (first signal), based on the operation on the push button 74, and outputs the electric signal to a signal converter 82. Thus, the first sensor switch 68a is configured in such a manner that switching can be performed between the ON and OFF states, and outputs the electric signal (first signal) according to the ON or OFF state.

An integrated circuit including a magnetic detection device such as a Hall element is used for the detector 72. When the intensity (physical quantity) of a magnetic field detected by a Hall element exceeds a predetermined threshold value, the integrated circuit outputs a predetermined voltage (first signal) corresponding to an energy supply start signal. Accordingly, the detector 72 converts the amount of change in physical quantity detected by the detector 72 into an amount of voltage as an electric signal, and outputs the electric signal to the signal converter 82. On the other hand, when the intensity of the magnetic field detected by the Hall element falls below a predetermined threshold value, the integrated circuit outputs a predetermined voltage (first signal) corresponding to an energy supply stop signal. The detector 72 is not limited to an integrated circuit including a Hall element, and may be a reed switch, an AMR sensor, or any other non-contact sensor.

The push button 74 includes a detection object 76 via which an operation on the push button 74 is detected by the detector 72, and a biasing body 78 such as a coil spring that biases the detection object 76 in a state separated from the detector 72. It is preferable that a material that is as soft as possible is used as the biasing body 78, in such a manner that the detection object 76 can be easily made close to the detector 72, compared to when a mechanical switch is operated. For example, a magnet is used for the detection object 76. The magnet used as the detection object 76 is, for example, a neodymium magnet. The magnet that can be used as the detection object 76 is not limited to a neodymium magnet, and may be other types of magnets such as a samarium-cobalt magnet, a ferrite magnet, and an Al—Ni—Co magnet. The push button 74 is an example of an operation portion.

It is preferable that the second sensor switch 68b is formed in a manner similar to the first sensor switch 68a. Accordingly, the second sensor switch 68b allows switching between the ON and OFF states, in a manner similar to the first sensor switch 68a, and outputs an electric signal as a first signal according to the ON or OFF state.

In the switch detector 28 of the energy generator 16 according to the present embodiment, circuits (e.g., photocouplers) with a configuration similar to that of the first mechanical switch 48a are arranged, in such a manner that the number of the circuits is equal to the number of switches. Thus, the switch detector 28 cannot directly detect a signal in response to an operation on the first sensor switch 68a and the second sensor switch 68b, namely, a predetermined voltage (first signal) output from the detector 72. Accordingly, the switch detector 28 does not recognize a signal (first signal) directly input from the first sensor switch 68a or the second sensor switch 68b.

Figure 4:
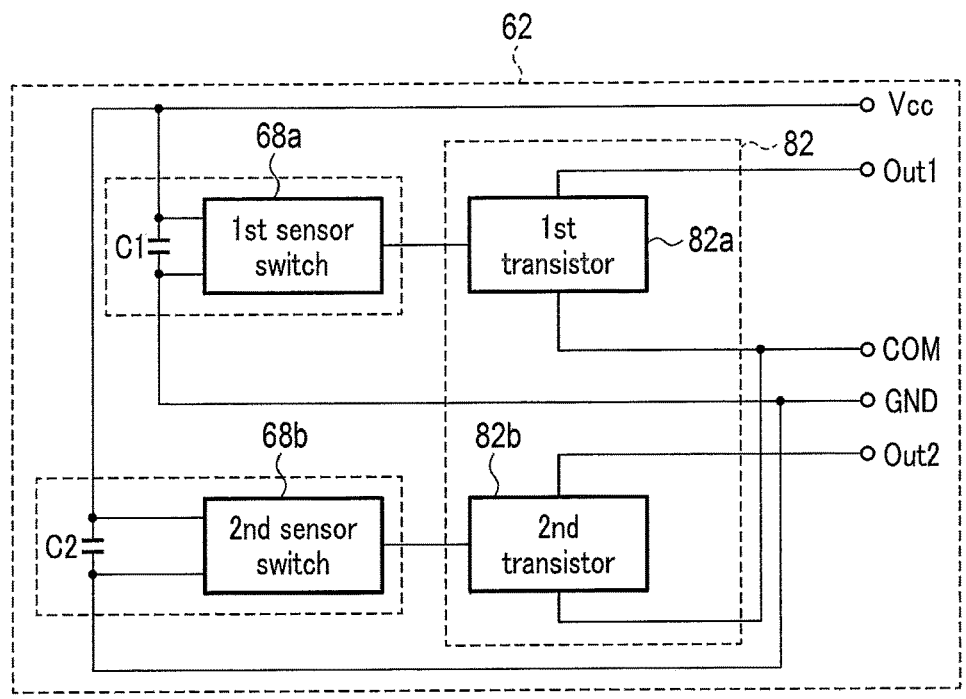
FIG. 4 is a schematic diagram showing a circuit configuration of first and second sensor switches and a signal converter, which are arranged in a housing of a second treatment instrument of the medical system according to the first embodiment.

As shown in FIG. 4, the second treatment instrument 14 includes the signal converter 82 provided between the first and second sensor switches 68a and 68b and the connector 66. Thus, the signal converter 82 is provided in the housing 62. Transistors (digital transistors) 82a and 82b, for example, are used as the signal converter 82.

A power-supply terminal Vcc is connected to one end of the first sensor switch 68a. A ground terminal GND is connected to the other end of the first sensor switch 68a. The power-supply terminal Vcc that is connected to the first sensor switch 68a is also connected to one end of the second sensor switch 68b. The ground terminal GND that is connected to the first sensor switch 68a is also connected to the other end of the second sensor switch 68b. A power-supply voltage Vcc is supplied to the power-supply terminal Vcc, and a ground voltage is supplied to the ground terminal GND. A suitable voltage (e.g., 5 V) to drive the sensor switches 68a and 68b is applied between the power-supply voltage Vcc and the ground terminal GND. The capacitors C1 and C2 of the sensor switches 68a and 68b are provided for stabilization of the power-supply voltage Vcc between the power-supply terminal Vcc and the ground terminal GND, and are not necessarily used.

The first sensor switch 68a outputs a voltage (first signal) of 5 V, for example, when switched to OFF (a state in which the detection object 76 is separated from the detector 72) by the power-supply voltage Vcc. The first sensor switch 68a outputs a voltage (first signal) of 0 V when switched to ON (a state in which the detection object 76 is made to be in close proximity to the detector 72) by the power-supply voltage Vcc. Similarly, when the second sensor switch 68b is switched to OFF (a state in which the detection object 76 is separated from the detector 72), the second sensor switch 68b outputs a voltage (first signal) of, for example, 5 V, as shown in FIG. 1. The second sensor switch 68b outputs a voltage (first signal) of 0 V when switched to ON (a state in which the detection object 76 is made to be in close proximity to the detector 72). That is, the first sensor switch 68a and the second sensor switch 68b allow switching between ON and OFF states, and output a first signal (0 V or 5 V) according to the ON or OFF state.

The first sensor switch 68a is connected to the signal converter 82, as shown in FIG. 4. A first transistor 82a, for example, is used as the signal converter 82. The first transistor 82a is connected to a first output terminal Out1 and a common terminal (output terminal) COM. The second sensor switch 68b is connected to the signal converter 82. A second transistor 82b, for example, is used as the signal converter 82. The second transistor 82b is connected to the second output terminal Out2 and the common terminal COM. Accordingly, the common terminal COM is used in common by the signal converter 82 of the first sensor switch 68a and the second sensor switch 68b.

The signal converter 82 flows or not flows the current (second signal) from the first transistor 82a in response to the ON or OFF state of the first sensor switch 68a, and outputs the same state as the open or closed state of the first mechanical switch 48a to the switch detector 28. When the signal converter 82 receives the output of the first signal (0 V or 5 V), the signal converter 82 converts the first signal (voltage in this case) into the second signal (current in this case) of a different system (with a different content), and outputs the second signal to the outside (the energy generator 16) capable of detecting the second signal.

In a state in which the push button 74 of the first sensor switch 68a is not operated by the user (see FIG. 3A), the detection object 76 is separated from the detector 72 (OFF state), and a predetermined voltage (e.g., 5 V) is output to the first transistor 82a as the first signal. At this time, a current (second signal) does not flow between the first output terminal Out1 and the common terminal COM of the first transistor 82a. Accordingly, a current does not flow through the switch detector 28 of the energy generator 16 connected to the first treatment instrument 12.

When the push button 74 of the first sensor switch 68a is operated by the user, the detection object 76 changes from the state of being separated from the detector 72 (see FIG. 3A) to the state of being close thereto (see FIG. 3B), and the amount of change of the magnetic field exceeds a threshold value, the first sensor switch 68a is switched to ON. When the first sensor switch 68a is switched to ON, a predetermined voltage (e.g., 0 V) is output from the first sensor switch 68a to the first transistor 82a as the first signal. When the first sensor switch 68a is switched to ON, a current (second signal) flows between the output terminal Out1 and the common terminal COM of the first transistor 82a. Thereby, a current flows to the switch detector 28 of the energy generator 16 connected to the second treatment instrument 14. The ON/OFF operation of the first sensor switch 68a can be detected by the switch detector 28 of the energy generator 16, using the signal converted by the converter 82 arranged in the housing 62. The switch detector 28 of the energy generator 16 receives and detects the second signal output from the second treatment instrument 14. On the basis of the signal (second signal) detected by the switch detector 28, energy is output to the second treatment instrument 14 from the output portion 26 of the energy generator 16.

Similarly, when the push button 74 of the second sensor switch 68b is operated by the user, the detection object 76 changes from the state of being separated from the detector 72 to the state of being close thereto, and the amount of change of the magnetic field exceeds a threshold value, the second sensor switch 68b is switched to ON. When the second sensor switch 68b is switched to ON, a predetermined voltage (e.g., 0 V) is applied to the second transistor 82b. When the second sensor switch 68b is switched to ON, a current flows between the output terminal Out2 and the common terminal COM of the second transistor 82b. Thereby, a current flows to the switch detector 28 of the energy generator 16 connected to the second treatment instrument 14. The ON/OFF operation of the second sensor switch 68b can be detected by the switch detector 28 of the energy generator 16, using the signal converted by the converter 82 arranged in the housing 62.

The first treatment instrument 12 can be suitably used even when the connector 46 of the first treatment instrument 12 is connected to another female connector 30b of the energy generator 16. Moreover, the second treatment instrument 14 can be suitably used even when the connector 66 of the second treatment instrument 14 is connected to another female connector 30a of the energy generator 16.

According to the medical system 10 of the present embodiment, the same type of signal is input to the switch detector 28 of the energy generator 16 in both of the state in which the first mechanical switch 48a and the second mechanical switch 48b of the first treatment instrument 12 are operated, and the state in which the first sensor switch 68a and the second sensor switch 68b of the second treatment instrument 14 are operated. That is, even though the switches 68a and 68b that output signals of various systems are used, it is possible to provide the treatment instrument (medical device) 14 that is applicable to the energy generator 16 including the switch detector 28 that detects signals of the minimum number of systems. It is thus possible to provide the medical device 14 capable of outputting certain signals that can be recognized by the energy generator 16 including the switch detector 28 that detects signals of the minimum number of systems. Accordingly, even when the treatment instruments 12 and 14 including the switches 48a, 48b, 68a, and 68b of different systems are used, the circuit of the switch detector 28 of the energy generator 16 does not need to be made complex by using in the housing 62 the same system for signals output from the connectors 46 and 66. According to the medical system 10, it is thus possible to reduce the size of the switch detector 28. According to the medical system 10, it is possible to reduce the number of switch detectors 28 and to use the same type of components for the female connectors 30a and 30b, thus reducing the manufacturing cost of the energy generator 16.

This allows the user to use the treatment instruments 12 and 14 for the energy generator 16, without being bothered by the types of the female connectors 30a and 30b compatible with the treatment instruments 12 and 14. By converting the output signals of the switches 68a and 68b on the housing 62 into signals of a suitable system after bringing the energy generator 16 on the market, a new switch structure (a switch that outputs a signal of a new system), which is not shown, can be used, without changing the system of the energy generator 16. Since the switch detector 28 of the energy generator 16 has no limitation about its switch configuration, it is possible to provide an optimum operation performance according to the shape and intended use of the treatment instrument.

Figure 5:
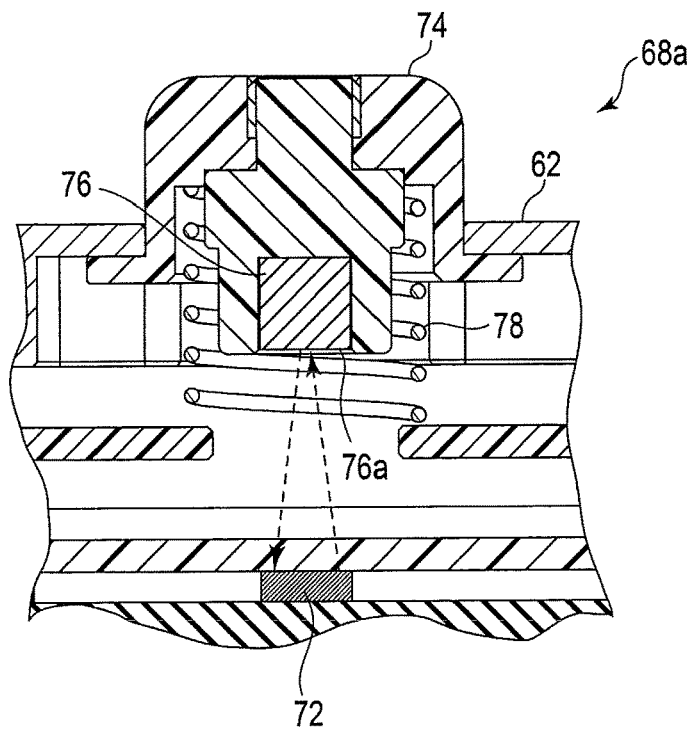
FIG. 5 is a vertical cross-sectional view schematically showing an example of the sensor switch used in the treatment instrument of the medical system in an OFF state, in particular, with a configuration different from that of FIG. 3A, according to the first and second embodiments.

In the present embodiment, magnetization is used in the sensor switches as an example. However, infrared rays may be used instead, as shown in FIG. 5.

For example, an element (chip) integrally including a transmitter and a receiver capable of transmitting and receiving infrared rays is used for the detector 72. For example, an infrared LED is used for the transmitter. The receiver is configured by, for example, a photodiode. The receiver is not limited to a photodiode, and may be any element configured to receive infrared rays, such as a phototransistor, a photo IC, a thermoelectric element, and a pyroelectric element. Accordingly, the detector 72 is capable of transmitting and receiving infrared rays.

On the other hand, the detection object 76 is capable of reflecting infrared rays. For example, a reflector (reflection plate) 76a capable of reflecting infrared rays from the detector 72 is used for the detection object 76. For example, a resin material that is polished to a mirror-smooth surface is used for the reflector 76a. A thermoplastic resin having a heat distortion temperature of, for example, less than 100° C. is used for the resin material of the reflector 76a.

Next, the functioning at the time of operating the push button 74 will be briefly explained. In a state before the user pushes the push button 74, the detector 72 detects that a distance to the detection object 76 is equal to or greater than a threshold value, and the signal converter 82 converts it into a suitable signal of a system that is the same as that of the mechanical switches, and transmits an OFF signal to a controller (control circuit) 22 of the energy generator 16.

When the user pushes the push button 74, the detector 72 detects that a distance to the detection object 76 is equal to or less than a threshold value on the basis of, for example, an optical path length (physical quantity), and transmits an ON signal to the controller 22 of the energy generator 16. That is, the detector (sensor) 72 converts an amount of change of the physical quantity detected by the detector 72 into an amount of voltage as an electric signal, and outputs it to the signal converter 82. The controller 22 performs a process in response to the ON signal.

On the other hand, when the user releases his or her finger from the push button 74, the detector 72 detects that a distance to the detection object 76 has become equal to or greater than a threshold value again, and transmits an OFF signal to the controller 22 of the energy generator 16.

(First Modification)

Figure 6:
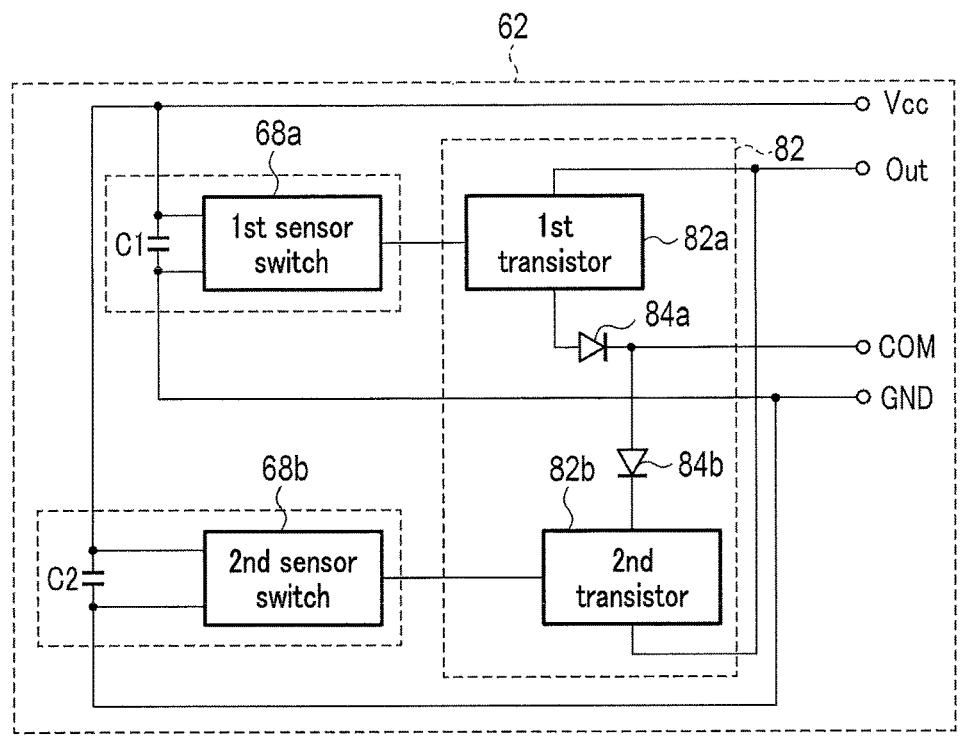
FIG. 6 is a schematic diagram showing a circuit configuration of first and second sensor switches and a signal converter, which are arranged in a housing of a second instrument of a medical system according to a first modification of the first embodiment.

As shown in FIG. 4, the first embodiment has been explained with respect to the case where the signal converter 82 includes two output terminals Out1 and Out2. However, the output terminals Out1 and Out2 may be unified, while using the common terminal COM in common, as shown in FIG. 6. That is, even when one treatment instrument 14 includes two sensor switches 68a and 68b, the output terminals may be unified into one output terminal Out. Accordingly, the signal converter 82 includes terminals (an output terminal Out and a common terminal (output terminal) COM) that are used in common to convert a first signal output from each of the first sensor switch 68a and the second sensor switch 68b into a second signal, and output the second signal to the outside (an energy generator 16).

As shown in FIG. 6, a first diode 84a is connected to a first transistor 82a, and a second diode 84b is connected to a second transistor 82b. An output from the second transistor 82b may be connected to the output terminal Out, which is used in common with the first transistor 82a. Thus, ON and OFF of the two sensor switches 68a and 68b can be output from the one output terminal Out as signals similar to those of the mechanical switches, using the first diode 84a and the second diode 84b.

Figure 7:
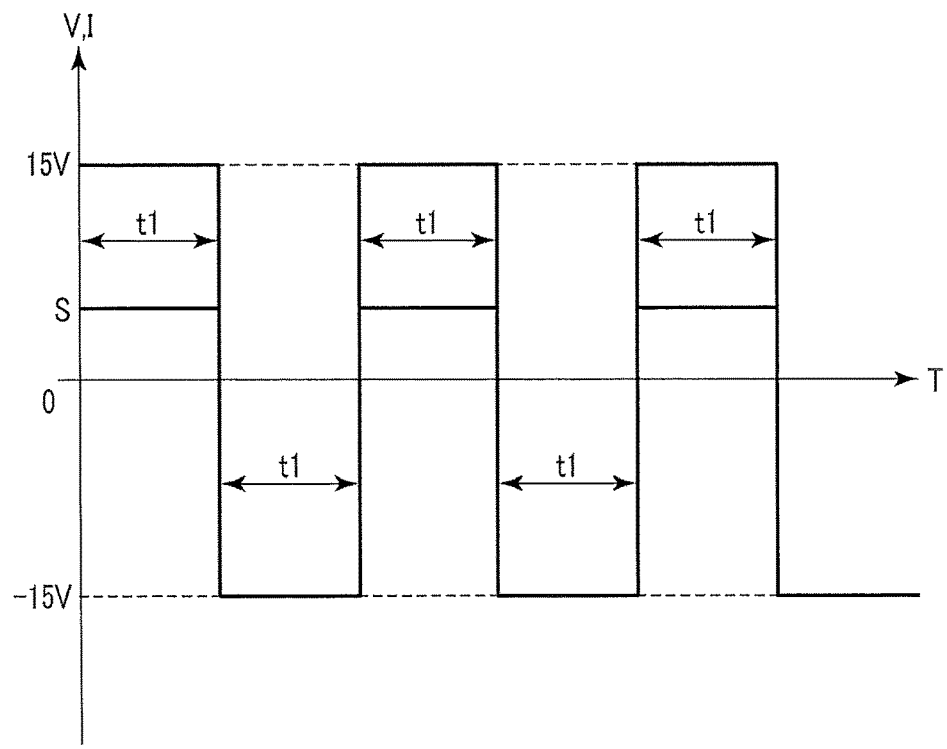
FIG. 7 is a schematic diagram showing an example of a toggle signal input to the signal converter arranged in the housing of the second treatment instrument of the medical system, where the lateral axis represents time and the vertical axis represents a voltage, and an example of a second signal where the vertical axis represents a current, according to the first modification of the first embodiment.

Here, a switch detector 28 of the energy generator 16 transmits a toggle signal that is used to distinguish between the switches 68a and 68b, as shown in FIG. 7, between the output terminal Out and the common terminal COM of the signal converter 82. The toggle signal refers to a signal that periodically reverses the positive or negative polarity of the voltage between the output terminal Out and the common terminal COM of the signal converter 82. Here, the switch detector 28 inputs a voltage of ±15 V as a toggle signal between the output terminal Out and the common terminal COM of the signal converter 82, by switching the voltage every predetermined period of time t1 (e.g., several milliseconds or several seconds), as shown in FIG. 7. When neither a plus signal (second signal) nor a minus signal (second signal), for example, is input to the switch detector 28 of the energy generator 16 via the common terminal COM while a toggle signal is transmitted between the output terminal Out and the common terminal COM of the signal converter 82, a controller 22 of the energy generator 16 determines that both of the first sensor switch 68a and the second sensor switch 68b are in the OFF state. When a plus signal (a current of a suitable plus value) S is input to the switch detector 28 from the first transistor 82a via the common terminal COM while a plus toggle signal (+15 V), for example, is input, the controller 22 of the energy generator 16 determines that the first sensor switch 68a is switched to ON. Although not shown, when a minus signal (a current of a suitable minus value) is input to the switch detector 28 from the second transistor 82b via the common terminal COM while a minus toggle signal (−15 V), for example, is input, the controller 22 of the energy generator 16 determines that the second sensor switch 68b is switched to ON. Thus, the controller 22 of the energy generator 16 is configured to detect ON/OFF of the first sensor switch 68a and the second sensor switch 68b via one output terminal Out and one common terminal COM, in response to an input signal to the switch detector 28 of the energy generator 16.

(Second Modification)

Figure 8:
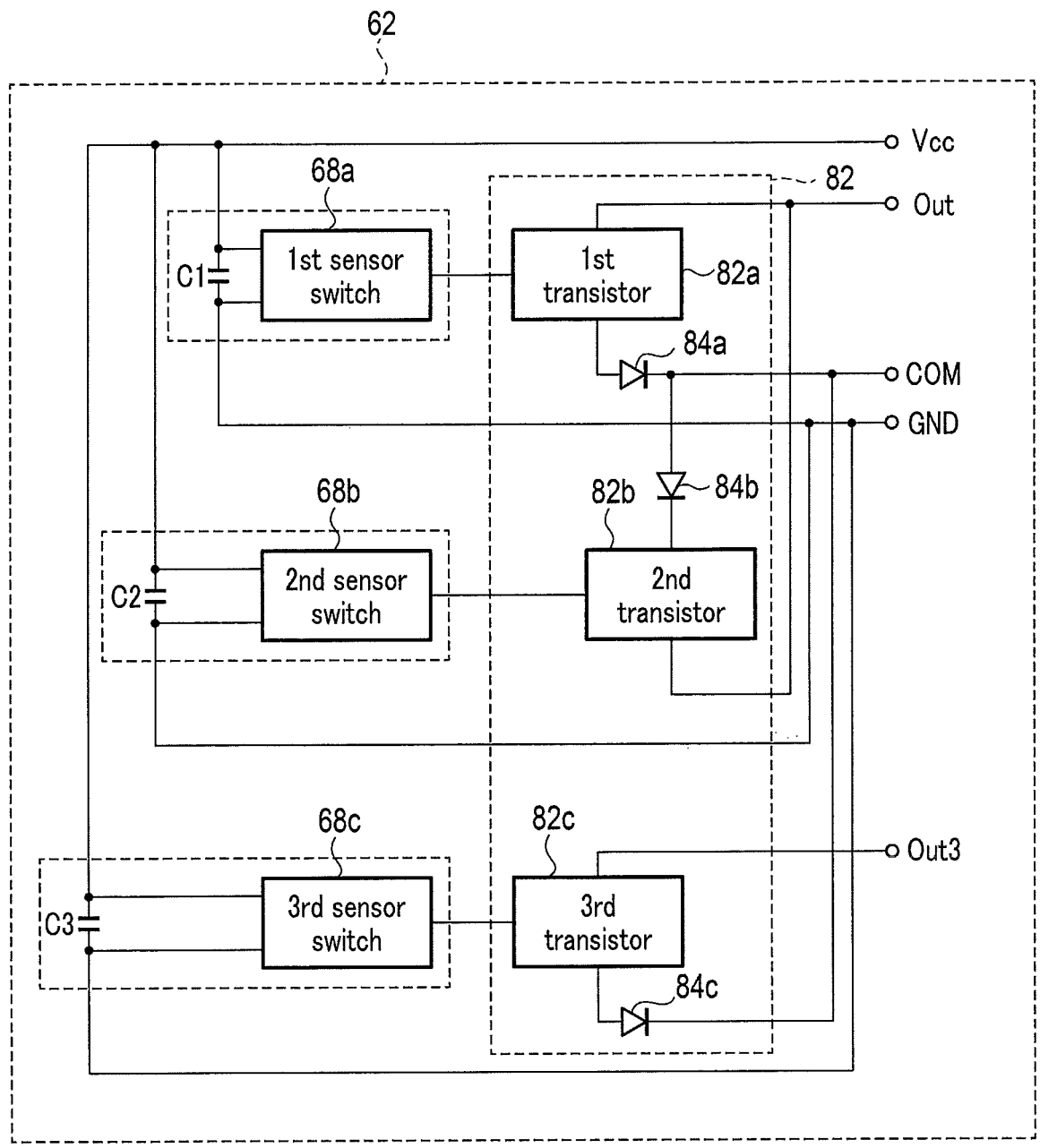
FIG. 8 is a schematic diagram showing a circuit configuration of first to third sensor switches and a signal converter, which are arranged in a housing of a second instrument of a medical system according to a second modification of the first embodiment.

An example will be explained in which three sensor switches 68a, 68b and 68c are provided, as shown in FIG. 8.

In this case, the circuitry in the housing 62 may be obtained by extending the circuitry of the first modification shown in FIG. 6. A third sensor switch 68c, a third transistor 82c that serves as a signal converter 82, and a diode 84c is provided in the housing 62.

When the three sensor switches 68a, 68b, and 68c are provided on the housing 62, one end of the third sensor switch 68c is connected to a power-supply terminal Vcc, and the other end is connected to a ground terminal GND. The third transistor 82c is connected to an output terminal Out3, and is also connected to a common terminal COM.

The third sensor switch 68c outputs 5 V (first signal) in the OFF state, and outputs 0 V (first signal) when switched to ON, in a manner similar to the first sensor switch 68a and the second sensor switch 68b described with reference to the first embodiment. In this case, when the third sensor switch 68c is switched to OFF, the third transistor 82c blocks a current (second signal) from flowing between the common terminal COM and the third output terminal Out3. When the third sensor switch 68c is switched to ON, the third transistor 82c lets a current (second signal) flow between the common terminal COM and the third output terminal Out3.

Second Embodiment

Next, a second embodiment will now be described with reference to FIGS. 9 and 10. The present embodiment is a modification of the first embodiment, including all the modifications mentioned above. Elements that are the same as those described in connection with the first and second embodiments or that have the same functions as those described in connection with the first and second embodiments will be assigned with the same reference symbols, and detailed descriptions of such elements will be omitted.

In the first embodiment, an example has been explained in which the signals output from the mechanical switches 48a and 48b of the first treatment instrument 12 are directly detected by the switch detector 28 (see FIG. 2) of the energy generator 16, and the signals output from the sensor switches 68a and 68b of the second treatment instrument 14 are converted into the signals similar to those of the mechanical switches on the housing 62, in such a manner that the converted signals can be detected by the switch detector 28 (see FIG. 2) of the energy generator 16. In this embodiment, as shown in FIG. 9, signals output from mechanical switches 48a and 48b of a first treatment instrument 12 are converted into signals similar to those of sensor switches in a housing 42, in such a manner that the converted signals can be detected by a switch detector 28 (see FIG. 2) of an energy generator 16. The signals output from sensor switches 68a and 68b of a second treatment instrument 14 can be directly detected by the switch detector 28 (see FIG. 2) of the energy generator 16.

Figure 10:
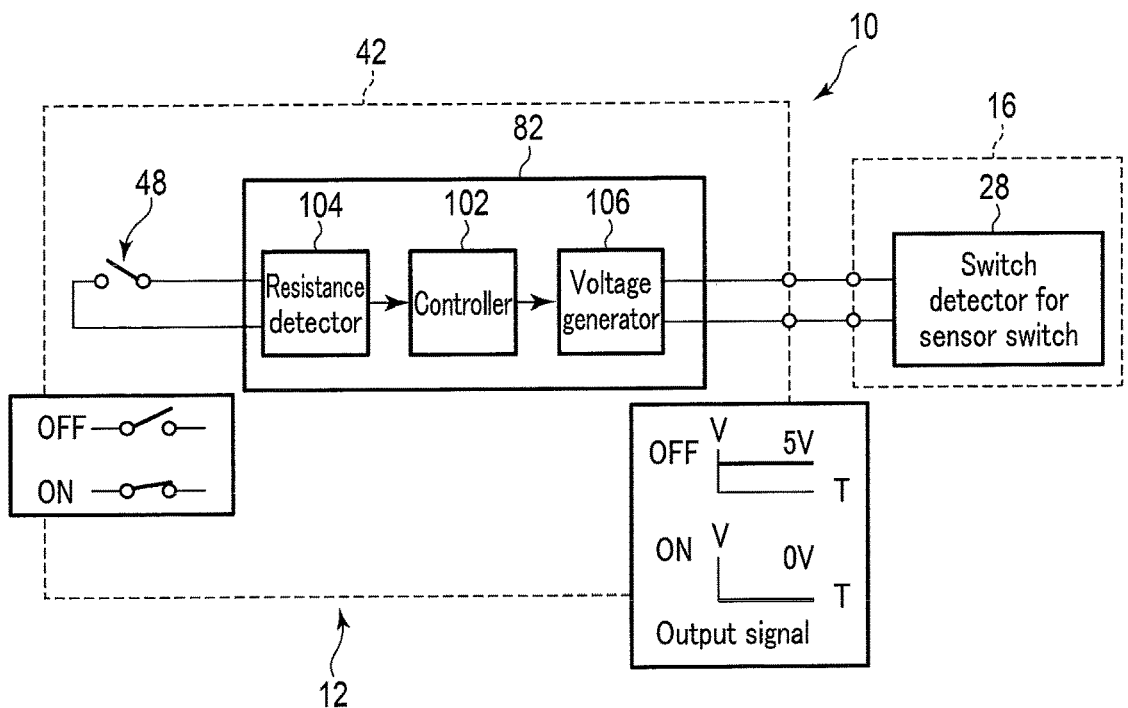
FIG. 10 is a schematic block diagram showing a state in which a signal (first signal) of a mechanical switch of a first treatment instrument of the medical system is converted into a voltage signal (second signal), in such a manner that the voltage signal can be detected by a switch detector, according to the second embodiment.

An example will be explained in which ON and OFF of the first mechanical switch 48a of the first treatment instrument 12 are converted into signals by a signal converter 82, as shown in FIG. 10. Unlike the first embodiment, the switch detector 28 of the energy generator 16 can directly detect a signal (0 V in the ON state and 5 V in the OFF state) output from the sensor switches 68a and 68b as a second signal, but cannot directly detect a signal (first signal) output from the first mechanical switch 48a.

The signal converter 82 includes a controller (processor) 102, a resistance detector 104, and a voltage generator 106. Although not shown, the signal converter 82 includes a power-supply terminal Vcc and a ground terminal GND, which operate the controller 102, the resistance detector 104, and the voltage generator 106. A suitable voltage is applied between the power-supply terminal Vcc and the ground terminal GND. The resistance value (first signal) of the resistance detector 104 is infinite when the first mechanical switch 48a is in the OFF state. The controller 102 determines that the first mechanical switch 48a is in the ON state by using, as a threshold value, a suitable resistance value (first signal) detected by the resistance detector 104 that is sufficiently smaller than infinity (e.g., a value sufficiently close to 0Ω relative to infinity). The controller 102 causes the voltage generator 106 to generate a potential difference on the basis of a change in resistance value (infinity or a value sufficiently close to 0Ω relative to infinity) detected by the resistance detector 104. As an example, let us assume that the first mechanical switch 48a outputs 5 V (second signal) in the OFF state, and outputs 0 V (second signal) in the ON state. That is, the signal converter 82 converts a change in resistance value of the first mechanical switch 48a as a first signal into a voltage as a second signal.

The switch detector 28 of the energy generator 16 detects switching between ON and OFF of the first mechanical switch 48a based on a voltage, and thereby the controller 22 determines whether the first mechanical switch 48a is switched to ON or OFF.

Similarly as in the switching of the first mechanical switch 48a, switching between ON and OFF of the second mechanical switch 48b can be detected based on a voltage by the switch detector 28 of the energy generator 16, by causing the signal converter 82 to convert a signal. Accordingly, the controller 22 is configured to determine whether the second mechanical switch 48b is switched to ON or OFF, in a manner similar to the first mechanical switch 48a.

According to the medical system 10 of the present embodiment, the same type of signal is input to the switch detector 28 of the energy generator 16 in both of the state in which the first mechanical switch 48a and the second mechanical switch 48b of the first treatment instrument 12 are operated, and the state in which the first sensor switch 68a and the second sensor switch 68b of the second treatment instrument 14 are operated. That is, even though the switches 48a and 48b that output signals of various systems are used, it is possible to provide the treatment instrument (medical device) 12 that is applicable to the energy generator 16 including the switch detector 28 that detects signals of the minimum number of systems. It is thus possible to provide the medical device 12 configured to output certain signals that can be recognized by the energy generator 16 including the switch detector 28 that detects signals of the minimum number of systems.

(Modification)

Figure 11:
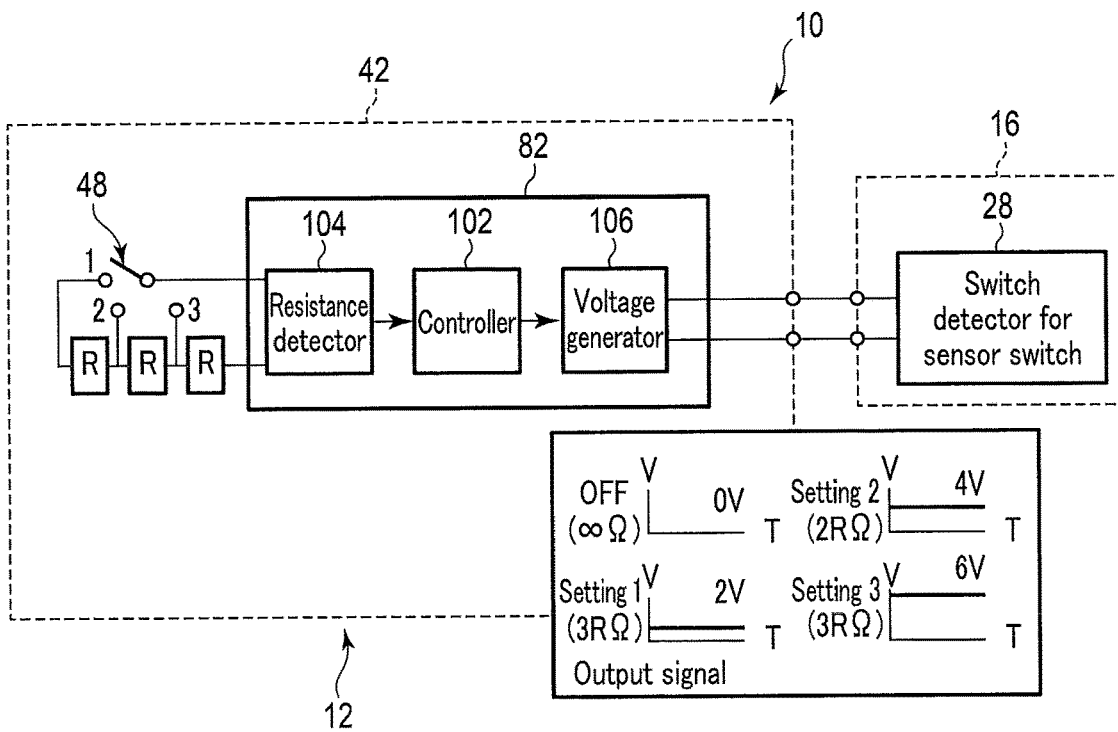
FIG. 11 is a schematic block diagram showing a state in which a signal (first signal) of a mechanical switch of a first treatment instrument of a medical system is converted into a voltage signal (second signal), in such a manner that the voltage signal can be detected by a switch detector, according to a modification of the second embodiment.

A case will be explained where the mechanical switch 48 is configured in such a manner that a state can be selected from (switching can be made between) a plurality of states (ON1, ON2, ON3 and OFF) by means of sliding, for example, as shown in FIG. 11.

When the mechanical switch 48 is switched to OFF, the resistance of the resistance detector 104 becomes infinite. In this case, the voltage generator outputs 0 V (second signal). When the mechanical switch 48 is switched to ON1, the resistance detector 104 detects series resistances 3R. In this case, the voltage generator 106 outputs 2 V (second signal), for example, as an output signal. When the mechanical switch 48 is switched to ON2, the resistance detector 104 detects series resistances 2R. In this case, the voltage generator 106 outputs 4 V (second signal), for example, as an output signal. When the mechanical switch 48 is switched to ON3, the resistance detector 104 detects a series resistance R. In this case, the voltage generator 106 outputs 6 V (second signal), for example, as an output signal.

The mechanical switch 48 allows switching between a plurality of states (ON1, ON2, ON3, and OFF) using a switch detector 28, and the state of the mechanical switch 48 switched to ON1, ON2, ON3, or OFF can be detected based on a voltage.

Third Embodiment

Figure 12:
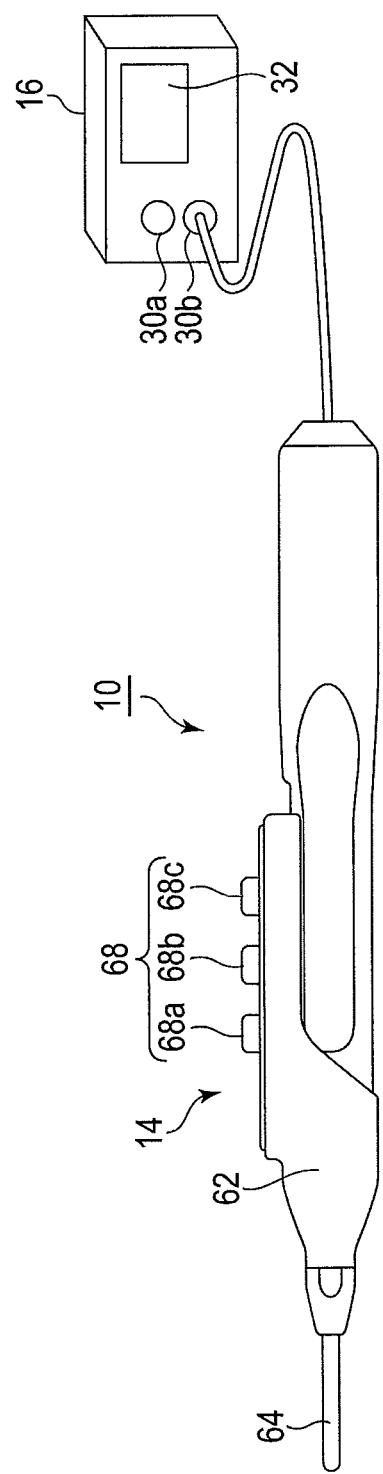
FIG. 12 is a schematic diagram showing a medical system according to a third embodiment.

Next, a third embodiment will now be described with reference to FIG. 12. The present embodiment is a modification of the first and second embodiments, including all the modifications mentioned above. Elements that are the same as those described in connection with the first embodiment or that have the same functions as those described in connection with the first embodiment will be assigned with the same reference symbols, and detailed descriptions of such elements will be omitted.

When the second treatment instrument 14 includes three switches 68a, 68b, and 68c, there may be a difference in frequency in use. When one of the three switches 68a, 68b, and 68c is a switch for various settings, a sensor switch is not necessarily used. In this case, the switch 68c may be a mechanical switch, instead of a sensor switch. When a mechanical switch is used as the switch 68c, a tactile switch or a slide switch may be used. Suitably operating the (mechanical) switch 68c requires a large amount of force, compared to the amount of force required for the sensor switches 68a and 68b adjacent thereto, and the difference between such amounts of forces is large. This suppresses a malfunction of simultaneously operating the switches 68b and 68c.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A medical system comprising:
a medical device comprising:
   a housing;
   a switch provided on the housing, and the switch being configured to allow switching between a plurality of states and being configured to output a first signal in response to one of the states to which the switching is performed; and
   a converter provided in the housing, the converter being configured to convert the first signal into a second signal of a different system when the converter receives the output of the first signal, and being configured to output the second signal to an energy generator configured to detect the second signal;
the energy generator, the energy generator connected to the medical device, and including:
   a detector that is configured to receive the second signal output from the medical device and detects the received signal and
   an output portion that is configured to output energy to the medical device based on the received signal detected by the detector; and
another medical device connected to the energy generator, the another medical device including:
   another housing different from the housing, and
   another switch provided on said another housing and being configured to allow switching between the plurality of states and being configured to output the second signal to the detector of the energy generator in response to the states,
wherein the output portion of the energy generator is configured to output energy to said another medical device based on the received signal detected by the detector.

2. The medical system according to claim 1, wherein the switch is configured to output an electric signal as the first signal from a sensor to the converter.

3. The medical system according to claim 2, wherein the sensor is configured to convert an amount of change of a physical quantity detected by the sensor into an amount of voltage as the electric signal, and outputs the electric signal to the converter.

4. The medical system according to claim 1, wherein the switch includes an input portion and a sensor that outputs an electric signal as the first signal based on an operation on the input portion.

5. The medical system according to claim 1, comprising an additional switch provided on the housing, and said additional switch being configured to allow switching between the plurality of states and being configured to output the first signal in response to one of the states to which the switching is performed,
wherein the converter includes output terminals used in common to convert the first signal output from each of the switches and said additional switch into the second signal, and outputs the second signal to the energy generator.

6. The medical system according to claim 5, wherein:
a toggle signal that is used to distinguish between the switch and said another switch is input between the output terminals, and
the converter is configured to output a signal based on an operation on the switch and said additional switch as the second signal, in response to the toggle signal.

7. The medical system according to claim 1, wherein:
the switch is a mechanical switch, and the converter is configured to convert a change in resistance value as the first signal of the mechanical switch into a voltage as the second signal.

8. The medical system according to claim 1, comprising another switch provided on the housing, and said another switch being configured to allow switching between the plurality of states and being configured to output the second signal to the energy generator in response to one of the states to which the switching is performed.

9. The medical system according to claim 1, comprising a treatment portion to which energy is transmitted from the energy generator based on the one of the states of the switch to which the switching is performed.

10. The medical system according to claim 1, wherein the plurality of states of the switch are two states including ON and OFF.

11. The medical system according to claim 1, wherein the detector is configured to detect a change in current as the second signal.

12. The medical system according to claim 1, wherein the detector is configured to detect a change in voltage as the second signal.

* * * * *